United States Patent
Nolan et al.

(10) Patent No.: US 10,961,509 B2
(45) Date of Patent: Mar. 30, 2021

(54) ENGINEERED ENDOTHELIAL CELLS EXPRESSING AN ETS TRANSCRIPTION FACTOR

(71) Applicant: ANGIOCRINE BIOSCIENCE, INC., San Diego, CA (US)

(72) Inventors: Daniel Joseph Nolan, Hawthorne, NY (US); Paul William Finnegan, Del Mar, CA (US); Michael Daniel Ginsberg, San Diego, CA (US); Claude Geoffrey Davis, Auburn, CA (US)

( * ) Notice: Subject to any disclaimer, the term of this patent is extended or adjusted under 35 U.S.C. 154(b) by 0 days.

(21) Appl. No.: 15/746,397

(22) PCT Filed: Jul. 19, 2016

(86) PCT No.: PCT/US2016/042873
§ 371 (c)(1),
(2) Date: Jan. 19, 2018

(87) PCT Pub. No.: WO2017/015246
PCT Pub. Date: Jan. 26, 2017

(65) Prior Publication Data
US 2018/0195040 A1 Jul. 12, 2018

Related U.S. Application Data

(60) Provisional application No. 62/194,466, filed on Jul. 20, 2015.

(51) Int. Cl.
| | |
|---|---|
| *C12N 5/071* | (2010.01) |
| *A61K 35/44* | (2015.01) |
| *A61K 35/28* | (2015.01) |
| *A61K 38/16* | (2006.01) |
| *A61K 38/17* | (2006.01) |
| *C07K 14/005* | (2006.01) |
| *C07K 14/47* | (2006.01) |
| *C12N 5/0789* | (2010.01) |
| *C12N 7/00* | (2006.01) |
| *C12N 15/86* | (2006.01) |

(52) U.S. Cl.
CPC ............ *C12N 5/069* (2013.01); *A61K 35/28* (2013.01); *A61K 35/44* (2013.01); *A61K 38/162* (2013.01); *A61K 38/1709* (2013.01); *C07K 14/005* (2013.01); *C07K 14/47* (2013.01); *C12N 5/0647* (2013.01); *C12N 7/00* (2013.01); *C12N 15/86* (2013.01); *C12N 2500/90* (2013.01); *C12N 2501/60* (2013.01); *C12N 2501/998* (2013.01); *C12N 2502/1171* (2013.01); *C12N 2510/00* (2013.01); *C12N 2710/10322* (2013.01); *C12N 2740/15043* (2013.01)

(58) Field of Classification Search
None
See application file for complete search history.

(56) References Cited

U.S. PATENT DOCUMENTS

| | | | |
|---|---|---|---|
| 6,852,533 B1 | 2/2005 | Rafii et al. | |
| 7,396,680 B2 | 7/2008 | Shmelkov et al. | |
| 8,465,732 B2* | 6/2013 | Rafii | C07K 14/005 |
| | | | 424/93.21 |
| 8,785,192 B2* | 7/2014 | Yu | G01N 33/5064 |
| | | | 435/377 |
| 9,637,723 B2 | 5/2017 | Rafii et al. | |
| 2008/0014180 A1* | 1/2008 | Lanza | A61P 37/06 |
| | | | 424/93.7 |
| 2013/0224161 A1 | 8/2013 | Rafii et al. | |
| 2015/0361398 A1 | 12/2015 | Sandler et al. | |
| 2017/0137781 A1 | 5/2017 | Qiang et al. | |
| 2017/0181168 A1 | 10/2017 | Finnegan et al. | |
| 2017/0360988 A1 | 12/2017 | Ginsberg et al. | |
| 2018/0214488 A1 | 8/2018 | Finnegan et al. | |

FOREIGN PATENT DOCUMENTS

| | | | | |
|---|---|---|---|---|
| WO | 2012006440 A2 | 1/2012 | | |
| WO | WO-2013181326 A1 * | 12/2013 | ............ | A61K 35/44 |

OTHER PUBLICATIONS

Haro et al., Cloning of the murine ER71 gene (Etsrp71) and initial characterization of its promoter. Genomics 85 (2005) 493-502 (Year: 2005).*
Liu et al., Induction of hematopoietic and endothelial cell program orchestrated by ETS transcription factor EP71/ETV2 (EMBO, 2015, 16:654-670) (Year: 2015).*
Foubert et al., Coadministration of Endothelial and Smooth Muscle Progenitor Cells Enhances the Efficiency of Proangiogenic Cell-Based Therapy. Circ Res. 2008;103;751-760 (Year: 2008).*
Kobayashi et al., Role of Etv2-positive cells in the remodeling morphogenesis during vascular development. Genes to Cells (2013) 18, 704-721 (Year: 2013).*
Butler et al., "Development of a vascular niche platform for expansion of repopulating human cord blood stem and progenitor cells" Blood, 120, (2012), pp. 1344-1347.
Chotinantakul et al., "Hematopoietic StemCell Development, Niches, and Signaling Pathways," Bone Marrow Research (2012), vol. 2012, pp. 1-16.
Kobayashi et al., "Angiocrine factors from Akt-activated endothelial cells balance self-renewal and differentiation of haematopoietic stem cells." Nature Cell Biology 12, pp. 1046-1056 (2010).
Nolan et al., "Molecular Signatures of Tissue-Specific Microvascular Endothelial Cell Heterogeneity in Organ Maintenance and Regeneration," Developmental Cell 26, 204-219, Jul. 29, 2013.
O'Shea et al. "Adenoviral proteins mimic nutrient/growth signals to activate the mTOR pathway for viral replication"; The EMBO Journal (2005) 24, 1211-1221.

(Continued)

Primary Examiner — Arthur S Leonard
(74) Attorney, Agent, or Firm — Grimes & Yvon LLP (57) ABSTRACT

In some aspects the present invention relates to engineered endothelial cells, such as E40RF1+ ETV2+ engineered endothelial cells. In other aspects the present invention relates to methods of making such engineered endothelial cells, and methods of using such engineered endothelial cells, for example in co-culture applications.

12 Claims, 3 Drawing Sheets

(56) References Cited

OTHER PUBLICATIONS

Rafii et al., "Human ESC-derived hemogenic endothelial cells undergo distinct waves of endothelial to hematopoietic transition" Blood, Jan. 31, 2013, vol. 121, No. 5, pp. 770-780.
Rafii & Lyden, "Therapeutic stem and progenitor cell transplantation for organ vascularization and regeneration", Nature Medicine vol. 9, pp. 702-712 (2003).
Rafii et al., "Angiocrine functions of organ-specific endothelial cells", Nature, 529 , Jan. 21, 2016, pp. 316-325.
Seandel et al: "Generation of a functional and durable vascular niche by the adenoviral E4ORF1 gene"; Proceedings of the National Academy of Sciences (PNAS), 2008, vol. 105, No. 49. pp. 19288-19293.
Zhang et al. "Adenovirus E4 Gene Promotes Selective Endothelial Cell Survival and Angiogenesis via Activation of the Vascular Endothelial-Cadherin/Akt Signaling Pathway"; The Journal of Biological Chemistry (2004) vol. 279, No. 12, pp. 11760-11766.
Angiocrine Bioscience, Expansion Protocol Guidelines; http://angiocrinebioscience.com/wp-content/uploads/CD34+-Expansion-Protocol-Guidelines.pdf, pp. 1-8.
International Search Report for PCT/US16/42873.
Extended European Search Report for EP 16828393.5.
Lee et al., "ER71 Acts Downstream of BMP,Notch, and Wnt Signaling in Blood and Vessel Progenitor Specification Cell Stem Cell", 2: 497-507 (2008).
Lindgren, AG et al. "ETV2 expression increases the efficiency of primitive endothelial cell derivation from human embryonic stem cells." Cell Regeneration. Jan. 7, 2015. vol. 4, No. 1.
Sumanas et al., "Interplay among Etsrp/ER71, Scl, and Alk8 signaling controls endothelial and myeloid cell formation", Blood, 111: 4500-4510 (2008).
Kataoka et al., "Etv2/ER71 induces vascular mesoderm from Flk1+ PDGFRα+ primitive mesoderm" Blood, 118: 6975-6986 (2011).
De Val et al., "Transcriptional Control of Endothelial Cell Development" Dev Cell, 16: 180-195 (2009).
Sato et al., "Role of ETS family transcription factors in vascular development and angiogenesis", Cell Struct Funct, 26: 19-24 (2001).
Liu et al., "Genome-Wide Analysis of the Zebrafish ETS Family Identifies Three Genes Required for Hemangioblast Differentiation or Angiogenesis" Circ Res, 103: 1147-1154 (2008).
Pham et al., "Combinatorial function of ETS transcription factors in the developing vasculature" Dev Biol, 303: 772-783 (2007).
Choi et al., "Hematopoietic and Endothelial Differentiation of Human Induced Pluripotent Stem Cells" Stem Cells 27, 559-567 (2009).
Morita et al., "ETS transcription factor ETV2 directly converts human fibroblasts into functional endothelial cells" PNAS, 112, 160-165 (2015).
Ginsberg et al., "Efficient Direct Reprogramming of Mature Amniotic Cells into Endothelial Cells by ETS Factors and TGFβ Suppression" Cell, 151: 559-575 (2012).
Lelievre et al., "The Ets family contains transcriptional activators and repressors involved in angiogenesis" The International Journal of Biochemistry & Cell Biology, 33: 391-407 (2001)).
James et al., "Expansion and maintenance of human embryonic stem cell-derived endothelial cells by TGFβ inhibition is Id1 dependent" Nat. Biotech. 28, 161-166 (2010).
Prasain et al., "Differentiation of human pluripotent stem cells to cells similar to cord-blood endothelial colony-forming cells" Nat. Biotech. 32, 1151-1157 (2014).
Meadows et al. "Regulation of endothelial cell development by ETS transcription factors," Seminars in Cell & Developmental Biology, vol . 22, No. 9, Dec. 1, 2011 (Dec. 1, 2011), pp. 976-984.
Kita et al., "Ex vivo expansion of hematopoietic stem and progenitor cells: Recent advances;" World J. Hematol.; May 6, 2014; vol. 3(2); p. 18-28.
Kurian et al., "Conversion of human fibroblasts into angioblast-like multipotent progenitor cells;" Nat Methods; Jan. 2013; vol. 10(1); p. 77-83.
Notta et al., "Isolation of Single Human Hematopoietic Stem Cells Capable of Long-Term Multilineage Engraftment;" Nat. Methods. Jan. 2013; vol. 10(1): p. 77-83.
Pineault et al., "Advances in umbilical cord blood stem cell expansion and clinical translation;" Experimental Hematology; 2015; vol. 43; p. 498-513.
Wognum et al., Hematopoietic Stem & Progenitor Cells—Mini-Review; Stem Cell Technologies; www.stemcell.com; Document #29068 Version 6.0.0 Apr. 2015.
Kobayashi, K et al. Role of Etv2-positive cells in the remodeling morphogenesis during vascular development. Genes Cells. Jun. 24, 2013. vol. 18, No. 8; pp. 704-721.
Hayashi et al., "Endothelialization and Altered Hematopoiesis by Persistent ETV2 Expression in Mice." Exp. Hematol. 2012, vol. 40, pp. 738-750.

\* cited by examiner

ENGINEERED ENDOTHELIAL CELLS EXPRESSING AN ETS TRANSCRIPTION FACTOR

CROSS-REFERENCE TO RELATED APPLICATIONS

This application claims the benefit of priority of U.S. Provisional Patent Application No. 62/194,466 filed on Jul. 20, 2015, the contents of which are hereby incorporated by reference in their entireties.

INCORPORATION BY REFERENCE

For the purpose of only those jurisdictions that permit incorporation by reference, all of the references cited in this disclosure are hereby incorporated by reference in their entireties. In addition, any manufacturers' instructions or catalogues for any products cited or mentioned herein are incorporated by reference. Documents incorporated by reference into this text, or any teachings therein, can be used in the practice of the present invention. Many of the general teachings provided in U.S. Pat. No. 8,465,732 can be used in conjunction with the present invention, or can be adapted for use with the present invention. Accordingly, the entire contents of U.S. Pat. No. 8,465,732 are hereby expressly incorporated by reference into the present application.

BACKGROUND

Members of the E-twenty six or "ETS" family of transcription factors (TFs), including ETV2 (Lee et al., Cell stem cell, 2: 497-507 (2008); Sumanas et al., Blood, 111: 4500-4510 (2008)), FLI1 (Liu et al., Current Bio. 18: 1234-1240 (2008)), and ERG (McLaughlin et al., Blood, 98: 3332-3339 (2001)) have been implicated in regulating vascular development and angiogenesis (De Val et al., Dev Cell, 16: 180-195 (2009); Sato et al., Cell Struct Funct, 26: 19-24 (2001)). These TFs directly regulate the expression of genes associated with endothelial cell (EC) development and function. Adult ECs constitutively express several ETS factors, such as FLIT ERG (isoforms 1 and 2), ETSJ, ETS2, Elfl, Elkl, VEZF and ETV6, while ETV2 is transiently expressed during embryonic development and is absent in adult ECs (Kataoka et al., Blood, 118: 6975-6986 (2011); Lelievre et al., The International Journal Of Biochemistry & Cell Biology, 33: 391-407 (2001)). In addition to playing key roles in vascular specification during development (Liu et al., Circ Res, 103: 1147-1154 (2008); Pham et al., Dev Biol, 303: 772-783 (2007)), it has also been shown that transient expression of some of these TFs can reprogram pluripotent stem cells into endothelial cells or can reprogram/transdifferentiate other (non-pluripotent) cells types into endothelial cells (see, e.g. Choi et al., Stem Cells 27, 559-567 (2009), James et al., Nat. Biotech. 28, 161-166 (2010), Prasain et al., Nat. Biotech. 32, 1151-1157 (2014), Morita et al., PNAS, 112, 160-165 (2015), Kurian et al., Nat. Methods 10, 77-83 (2013), and Ginsberg et al., Cell, 151: 559-575). However, to the best of the inventors' knowledge, prior to the present invention, ETS family transcription factors, and in particular the ETV2 transcription factor, was not believed to have effects on differentiated endothelial cells or endothelial cells already committed to the endothelial cell lineage. Similarly, prior to the present invention, and to the best of the inventors' knowledge, it was also not expected that endothelial cells expressing such factors might have enhanced properties with regards to their ability to support the expansion of other cell types, such as stem and progenitor cells.

The adenoviral early 4 (E4) region contains at least 6 open reading frames (E4ORFs). The entire E4 region has been shown previously to regulate angiogenesis and promote survival of endothelial cells (see Zhang et al. (2004), J. Biol. Chem. 279(12):11760-66). It has also been shown previously that, within the entire E4 region, it is the E4ORF1 sequence that is responsible for these biological effects in endothelial cells. See U.S. Pat. No. 8,465,732. See also Seandel et al. (2008), "Generation of a functional and durable vascular niche by the adenoviral E4ORF1 gene," PNAS, 105(49):19288-93.

SUMMARY OF THE INVENTION

The present invention is based, in part, upon the discovery that the ETS transcription factor ETV2 has certain unexpected effects when expressed in endothelial cells, in particular when ETV2 is co-expressed with an adenovirus E4ORF1 polypeptide. While it was previously known that E4ORF1-expressing endothelial cells can be maintained in culture for extended time periods, even in the absence of serum, and can be used to support the culture of other cell types such as hematopoietic stem and progenitor cells (HSPCs) (see Kobayashi et al., Nature Cell Biology 12, 1046-1056 (2010); Butler et al., Blood 120, 1344-1347 (2012), it has now been discovered that engineered endothelial cells expressing both E4ORF1 and ETV2 (i.e. E4ORF1+ ETV2+ engineered endothelial cells) can also support HSPC expansion, and furthermore, that co-culture of HSPCs with E4ORF1+ ETV2+ endothelial cells leads to selective expansion of a more primitive HSPC population than is observed when either E4ORF1+ endothelial cells or ETV2+ endothelial cells are used. Building on these discoveries, the present invention provides E4ORF1+ ETV2+ engineered endothelial cells, compositions comprising these cells, and various methods of generating and using these cells.

In one embodiment the present invention provides a population of E4ORF1+ ETS+ engineered endothelial cells—i.e. a population of engineered endothelial cells that express an adenovirus E4ORF1 polypeptide and an ETS transcription factor polypeptide. Suitable ETS transcription factor polypeptides include FLI1, ERG (isoforms 1 and 2), ETSJ, ETS2, Elfl, Elkl, VEZF, ETV6, and ETV2. In preferred embodiments the ETS transcription factor is ETV2. Thus, in one preferred embodiment the present invention provides a population of E4ORF1+ ETV2+ engineered endothelial cells. In some such embodiments the engineered endothelial cells comprise a recombinant nucleic acid molecule that encodes the recited molecules, for example a recombinant nucleic acid molecule that encodes an ETS transcription factor polypeptide, or an ETV2 polypeptide, or an E4ORF1 polypeptide. In some such embodiments the recombinant nucleic acid molecule is in the form of a plasmid vector. In some such embodiments, the recombinant nucleic acid molecule is integrated into the genomic DNA of the engineered endothelial cells. In some embodiments the populations of engineered endothelial cells are isolated cell populations. In some embodiments the populations of engineered endothelial cells are substantially pure cell populations. In some embodiments the populations of engineered endothelial cells are present in vitro, for example in cell culture. In some embodiments the populations of engineered endothelial cells are present in vivo, for example in a living subject.

In some embodiments of the present invention the engineered endothelial cells are derived from differentiated endothelial cells. In some embodiments the engineered endothelial cells are derived from adult endothelial cells. In some embodiments the engineered endothelial cells are not embryonic endothelial cells, or are not derived from embryonic endothelial cells. In some embodiments the engineered endothelial cells are derived from human endothelial cells. In some embodiments the engineered endothelial cells are derived from primary endothelial cells. In some embodiments the engineered endothelial cells are derived from human umbilical vein endothelial cells (HUVECs).

In some embodiments the present invention provides compositions comprising the various endothelial cell populations described herein. For example, in one embodiment the present invention provides a composition comprising a population of engineered endothelial cells as described herein. In some embodiments such a composition may comprise a carrier solution, such as a physiological saline solution. In some embodiments such a composition may comprise other cell types, such as stem or progenitor cells, including, but not limited to hematopoietic stem or progenitor cells (HSPCs). In some embodiments the HSPCs are genetically modified. In some embodiments the compositions provided herein are therapeutic compositions and comprise cells, carrier solutions, and/or other components that are suitable for administration to living subjects, such as human subjects. In some embodiments such compositions may be used in a cell transplantation procedure, such as an HSPC transplantation procedure.

In those embodiments where the compositions (such as therapeutic compositions) comprise HSPCs, the HSPCs may be obtained or derived from any suitable source. For example, in one embodiment the HSPCs are obtained or derived from bone marrow. In another embodiment the HSPCs are obtained or derived from peripheral blood. In another embodiment the HSPCs are obtained or derived from amniotic fluid. In yet another embodiment the HSPCs are obtained from umbilical cord blood.

In some embodiments the present invention provides methods for maintaining or expanding endothelial cells in culture. For example, in one embodiment the present invention provides a method for maintaining or expanding endothelial cells in culture comprising: introducing a nucleic acid molecule encoding an ETS transcription factor polypeptide and a nucleic acid molecule encoding an E4ORF1 polypeptide into endothelial cells to produce E4ORF1+ ETS+ engineered endothelial cells, wherein the engineered endothelial cells can be maintained or expanded in culture. In some embodiments, the introduction of the above mentioned transcription factors will have durable effects and will only be required transiently, for example by expression by an inducible plasmid, purified protein, or peptidomimetic. In preferred embodiments the ETS transcription factor is ETV2 and the engineered endothelial cells produced are E4ORF1+ ETS+ engineered endothelial cells. Each of such methods may also comprise subsequently culturing the engineered endothelial cells. In some embodiments, such culturing may be performed in the absence of serum, or in the absence of exogenous growth factors, or in the absence of both serum and exogenous growth factors. In some embodiments the step of "introducing" the various nucleic acid molecules is performed by transfection, such as by liposome-mediated transfection, polybrene-mediated transfection, DEAE dextran-mediated transfection, electroporation, calcium phosphate precipitation, microinjection, or micro-particle bombardment. In other embodiments the step of "introducing" the various nucleic acid molecules is performed by viral-mediated transduction, for example lentivirus-mediated transduction, adenovirus-mediated transduction, retrovirus-mediated transduction, adeno-associated virus-mediated transduction or herpesvirus-mediated transduction. In some embodiments the step of "introducing" the various nucleic acid molecules is performed using one or more gene editing technologies, for example using zinc finger nucleases (ZFNs), Transcription Activator-Like Effector Nucleases (TALENs), the CRISPR/Cas system, and/or engineered meganuclease re-engineered homing endonucleases. In some such methods the endothelial cells used are primary endothelial cells. In some such methods the endothelial cells used are human endothelial cells, such as HUVECs.

In some embodiments the present invention provides various co-culture methods. For example, in one embodiment the present invention provides a method of maintaining or expanding a population of "cells of interest" in culture, the method comprising obtaining or generating a population of E4ORF1+ ETS+ engineered endothelial cells (such as, preferably, E4ORF1+ ETV2+ engineered endothelial cells), and culturing the engineered endothelial cells in the same culture vessel with a population of the cells of interest. In some embodiments, such co-culturing methods may be performed in the absence of serum, or in the absence of exogenous growth factors, or in the absence of both serum and exogenous growth factors. In some such embodiments the engineered endothelial cells form a feeder cell layer on the surface of the culture vessel. The "cells of interest" may be any cells for which it is desired to perform a co-culture with endothelial cells. For example, in one embodiment the cells of interest may be cancer cells, stem cells, progenitor cells or hybridoma cells. In one preferred embodiment the cells of interest are HSPCs. Importantly, it has been found that the co-culture methods described herein can lead to both improved expansion of HSPCs as compared to some other methods, and also can lead to greater expansion of more primitive HSPCs as compared to some other methods. Thus, in some embodiments the co-culture methods described herein are may be used to expand more primitive HSPCs, such as CD45RA− HSPCs, including CD34+high, CD45RA− HSPCs and CD34+high, CD38−low, Lin− HSPCs.

In some embodiments the present invention provides culture methods that employ conditioned medium obtained from the engineered endothelial cells of the invention. For example, in one embodiment the present invention provides a method for maintaining or expanding a population of cells of interest comprising obtaining conditioned medium from a culture of a population of E4ORF1+ ETS+ engineered endothelial cells (such as, preferably, E4ORF1+ ETV2+ engineered endothelial cells), and contacting the cells of interest with the conditioned medium. Similarly, in one embodiment the present invention provides a method for maintaining or expanding a population of cells of interest comprising: obtaining or generating a population of E4ORF1+ ETS+ engineered endothelial cells (such as, preferably, E4ORF1+ ETV2+ engineered endothelial cells), culturing the engineered endothelial cells in a culture vessel, collecting conditioned medium from the culture vessel, and contacting the cells of interest with the conditioned medium. Each of such methods may also include subsequently culturing the cells of interest.

Similarly, in some embodiments the present invention provides conditioned cell culture medium obtained from a culture of engineered endothelial cells of the invention. For example, in one embodiment the present invention provides a conditioned cell culture medium obtained from a culture of E4ORF1+ ETS+ engineered endothelial cells (such as, preferably, E4ORF1+ ETV2+ engineered endothelial cells).

In some embodiments the present invention also provides nucleic acid vector molecules. For example, in one embodiment the present invention provides a nucleic acid vector comprising both a nucleotide sequence encoding an ETS transcription factor polypeptide and a nucleotide sequence encoding an E4ORF1 polypeptide. In preferred embodiments the present invention provides a nucleic acid vector comprising both a nucleotide sequence encoding an ETV2 polypeptide and a nucleotide sequence encoding an E4ORF1 polypeptide. In some such embodiments the vector is an expression vector. In some such embodiments the vector is a lentiviral vector. In some such embodiments the vector is a retroviral vector. In some such embodiments the two nucleotide sequences are under the control of separate promoters. In other embodiments both nucleotide sequences are under the control of the same promoter.

The cell populations, compositions, and methods described herein may be useful in a variety of applications (as described further on other sections of this patent disclosure). In general, the engineered endothelial cells provided herein, and the related compositions and methods, can be used for any application in which other endothelial cells (e.g. naïve endothelial cells, or E4ORF1+ endothelial cells) are currently used or could be used, including, but not limited to, basic scientific research applications, cell culture methods (including co-culture methods), target discovery, drug discovery, and drug efficacy, toxicity, and/or safety testing. For example, in some embodiments the engineered endothelial cells may be used to facilitate the culture of other cell types, for example for the expansion of various types of stem or progenitor cells, such as HSCs. In some embodiments the engineered endothelial cells provided herein may be useful in therapeutic applications, including, but not limited to, in vivo cell transplantation procedures. For example, in some embodiments the engineered endothelial cells may themselves be administered to a subject, either alone or together with one or more additional cell types (including, but not limited to, stem or progenitor cells, such as HSCs).

These and other embodiments of the invention are described further in other sections of this patent disclosure. In addition, as will be apparent to those of skill in the art, certain modifications and combinations of the various embodiments described herein fall within the scope of the present invention.

DETAILED DESCRIPTION

The "Summary of the Invention," "Figures," "Brief Description of the Figures," "Examples," and "Claims" sections of this patent disclosure describe some of the main embodiments of the invention. This "Detailed Description" section provides certain additional description relating to the compositions and methods of the present invention, and is intended to be read in conjunction with all other sections of this patent disclosure. Furthermore, and as will be apparent to those in the art, the different embodiments described throughout this patent disclosure can be, and are intended to be, combined in various different ways. Such combinations of the specific embodiments described herein are intended to fall within the scope of the present invention.

Definitions

Certain definitions are provided below. Other terms are either defined elsewhere in this patent disclosure, have a meaning that is clear from the context in which they are used, or are used in accordance with their usual meaning in the art.

As used herein, the terms "about" and "approximately," when used in relation to numerical values, mean within + or −20% of the stated value.

The term "culturing" as used herein, refers to the propagation of cells on or in media of various kinds. "Co-culturing" refers to the propagation of two or more distinct types of cells on or in media of various kinds, for instance, in some embodiments, endothelial cells and hematopoietic stem or progenitor cells (HSPCs) may be co-cultured.

As used herein the term "effective amount" refers to an amount of a specified agent or cell population (e.g. an ETV2 or E4ORF1 polypeptide, a nucleic acid molecule encoding an ETV2 or E4ORF1 polypeptide, or a population of E4ORF1+ETV2+ engineered endothelial cells), as described herein, that is sufficient to achieve a detectable effect on one or more of the outcomes described herein. For example, in the case of expression of ETV2 and E4ORF1 in endothelial cells an effective amount of a nucleic acid molecule (e.g. in a vector) to be introduced/delivered to the endothelial cells may be one that results in a detectable increase in the endothelial cells survival or proliferation as compared to that of any suitable control (e.g. E4ORF1$^-$ ETV2$^-$ endothelial cells). In the case of use of E4ORF1+ ETV2+ endothelial cells in a co-culture method, an effect amount of the E4ORF1+ETV2+ endothelial cells may be one that results in a detectable expansion of the co-cultured cells, or that results in an increase in the expansion of the co-cultured cells as compared to that obtained with any suitable control (e.g. E4ORF1$^-$ETV2$^-$ endothelial cells). In the case of introduction of nucleic acid molecules encoding ETV2 and/or E4ORF1 into endothelial cells, an effective amount of the nucleic acid molecule (e.g. in a vector) may be one that results in a detectable increase in the endothelial cells survival or proliferation as compared to that of any suitable control (e.g. E4ORF1$^-$ETV2$^-$ cells). In the case of methods that involve administering E4ORF1$^+$ETV2$^+$ endothelial cells to a subject, an effective amount may be one that results in a detectable improvement of one or more desired biological or therapeutic indicators, (such as, for example, improved endothelial cell engraftment, improved endothelial/vascular regeneration, improved angiogenesis, improved survival or engraftment of a co-administered cell type, such as HSPCs, etc.), as compared to that of any suitable control (e.g. E4ORF1⁻ETV2⁻ endothelial cells). An appropriate "effective amount" in any individual case may be determined empirically, for example using standard techniques known in the art, such as dose escalation studies, and may be determined taking into account such factors as the planned use, the planned mode of delivery/administration, desired frequency of delivery/administration, etc. Furthermore, an "effective amount" may be determined using assays such as those described in the Examples section of this patent disclosure to assess effects endothelial cells or co-cultured cells.

The term "engineered" when used in relation to cells herein refers to cells that have been engineered by man to result in the recited phenotype (e.g. E4ORF1$^+$ETV2$^+$), or to express a recited nucleic acid molecule or polypeptide. The term "engineered cells" is not intended to encompass naturally occurring cells, but is, instead, intended to encompass, for example, cells that comprise a recombinant nucleic acid molecule, or cells that have otherwise been altered artificially (e.g. by genetic modification), for example so that they express a polypeptide that they would not otherwise express, or so that they express a polypeptide at substantially higher levels than that observed in non-engineered endothelial cells.

The terms "expansion" or "expanding" as used herein in the context of cells or cell culture refer to an increase in the number of cells of a certain type (for example endothelial cells or HSCs) from an initial population of cells, which may or may not be identical. The initial cells used for expansion need not be the same as the cells generated as a result of the expansion. For instance, the expanded cells may be produced by growth and differentiation of the initial population of cells.

"Genetic modification" or "gene-modified" refers to any addition, deletion or disruption of or to a cell's normal nucleotide sequences. In some embodiments, the endothelial cells described herein may, in addition to containing a nucleic acid molecule that encodes an ETS transcription factor polypeptide (such as ETV2) and a nucleic acid molecule that encodes an adenovirus E4ORF1 polypeptide, may also comprise one or more other genetic modifications—as desired. The term "genetic modification" encompasses use of a gene delivery vehicle and includes, but is not limited to, transduction (viral mediated transfer of nucleic acid to a recipient, either in vivo or in vitro), transfection (uptake by cells of isolated nucleic acid), liposome mediated transfer and others means well known in the art.

The term "hematopoietic stem cell" or "HSC" refers to a clonogenic, self-renewing pluripotent cell capable of ultimately differentiating into all cell types of the hematopoietic system, including B cells T cells, NK cells, lymphoid dendritic cells, myeloid dendritic cells, granulocytes, macrophages, megakaryocytes, and erythroid cells. As with other cells of the hematopoietic system, HSCs are typically defined by the presence of a characteristic set of cell markers.

The term "hematopoietic stem or progenitor cell" or "HSPC," as used herein, encompasses HSCs, as defined above, as well as multipotent non-self-renewing progenitor cells that are capable of ultimately differentiating into all cell types of the hematopoietic system, and oligopotent and unipotent progenitor cells capable differentiating into certain cell types of the hematopoietic system. HSPCs include CMPs, MPs, MEPs, and GMPs, each of which is defined elsewhere herein.

As used herein the term "isolated" refers to a product, compound, or composition which is separated from at least one other product, compound, or composition with which it is associated in its naturally occurring state, whether in nature or as made synthetically.

As used herein, the term "recombinant" refers to nucleic acid molecules that are generated by man (including by a machine) using methods of molecular biology and genetic engineering (such as molecular cloning), and that comprise nucleotide sequences that would not otherwise exist in nature. Thus, recombinant nucleic acid molecules are to be distinguished from nucleic acid molecules that exist in nature—for example in the genome of an organism. A nucleic acid molecule that comprises a complementary DNA or "cDNA" copy of an mRNA sequence, without any intervening intronic sequences such as would be found in the corresponding genomic DNA sequence, would thus be considered a recombinant nucleic acid molecule. By way of example, a recombinant E4ORF1 nucleic acid molecule might comprise an E4ORF1 coding sequence operatively linked to a promoter and/or other genetic elements with which that coding sequence is not ordinarily associated in a naturally-occurring adenovirus genome. Similarly, a recombinant ETV2 nucleic acid molecule might comprise an ETV2 cDNA sequence (i.e. a sequence that does not exist in nature in the genome of an organism), and/or may comprise ETV2-coding sequences operatively linked to a promoter and/or other genetic elements with which that coding sequence is not ordinarily associated in the genome of an organism.

The term "self-renewal" refers to the ability of a cell to divide and generate at least one daughter cell with the identical (e.g., self-renewing) characteristics of the parent cell. The second daughter cell may commit to a particular differentiation pathway. For example, a self-renewing hematopoietic stem cell divides and forms one daughter stem cell and another daughter cell committed to differentiation in the myeloid or lymphoid pathway. A committed progenitor cell has typically lost the self-renewal capacity, and upon cell division produces two daughter cells that display a more differentiated (i.e., restricted) phenotype.

The terms "subject" and "patient" are used herein interchangeably and refer to, except where indicated, mammals such as humans and non-human primates, as well as rabbits, rats, mice, goats, pigs, and other mammalian species.

The phrase "substantially pure" as used herein in relation to a cell population refers to a population of cells of a specified type (e.g. as determined by expression of one or more specified cell markers, morphological characteristics, or functional characteristics), or of specified types (plural) in embodiments where two or more different cell types are used together, that is at least about 50%, preferably at least about 75-80%, more preferably at least about 85-90%, and most preferably at least about 95% of the cells making up the total cell population. Thus, a "substantially pure cell population" refers to a population of cells that contain fewer than about 50%, preferably fewer than about 20-25%, more preferably fewer than about 10-15%, and most preferably fewer than about 5% of cells that are not of the specified type or types.

Nucleic Acid Molecules and Polypeptides

Several of the embodiments of the present invention described herein involve engineered endothelial cells that are E4ORF1+, ETS+, and/or ETV2+. E4ORF1+ cells express an adenovirus E4ORF1 polypeptide. ETS+ cells express an ETS transcription factor polypeptide (such as an ETV2 transcription factor polypeptide). ETV2+ cells express an ETV2 transcription factor polypeptide. These polypeptides are referred to collectively herein as "polypeptides of the invention").

The "polypeptides of the invention" are encoded by nucleic acid molecules. Thus, in some embodiments the present invention involves nucleic acid molecules that encode an adenovirus E4ORF1 polypeptide, nucleic acid molecules that encode an ETS transcription factor polypeptide, and/or nucleic acid molecules that encode an ETV2 transcription factor polypeptide. Such nucleic acid molecules are referred to collectively herein as "nucleic acid molecules of the invention."

The polypeptides of the invention and the nucleic acid molecules of the invention may have amino acid sequences or nucleotide sequences that are specified herein or known in the art, or may have amino acid or nucleotide sequences that are variants, derivatives, mutants, or fragments of such amino acid or nucleotide sequences—provided that such a variants, derivatives, mutants, or fragments have, or encode a polypeptide that has, one or more of the functional properties described herein (which include, but are not limited to, an ability to support the maintenance or expansion of endothelial cells in culture (e.g. in serum free conditions), and/or to support the expansion of another cell type in culture, such as HSPCs).

In those embodiments involving ETS transcription factor polypeptides, such as ETV2 polypeptides, the polypeptide may be any mammalian ETS transcription factor polypeptide, such as a human, non-human primate, rabbit, rat, mouse, goat, or pig polypeptide. In some preferred embodiments the polypeptide may be a human polypeptide. Amino acid sequences of such polypeptides, and nucleic acid sequences that encode such polypeptides, are well known in the art and available in well-known publicly available databases, such as the Genbank database.

In those embodiments involving adenovirus E4ORF1 polypeptides, the polypeptide sequence used may be from any suitable adenovirus type or strain, such as human adenovirus type 2, 3, 5, 7, 9, 11, 12, 14, 34, 35, 46, 50, or 52. In some preferred embodiments the polypeptide sequence used is from human adenovirus type 5. Amino acid sequences of such adenovirus polypeptides, and nucleic acid sequences that encode such polypeptides, are well known in the art and available in well-known publicly available databases, such as the Genbank database. For example, suitable sequences include the following: human adenovirus 9 (Genbank Accession No. CAI05991), human adenovirus 7 (Genbank Accession No. AAR89977), human adenovirus 46 (Genbank Accession No. AAX70946), human adenovirus 52 (Genbank Accession No. ABK35065), human adenovirus 34 (Genbank Accession No. AAW33508), human adenovirus 14 (Genbank Accession No. AAW33146), human adenovirus 50 (Genbank Accession No. AAW33554), human adenovirus 2 (Genbank Accession No. AP.sub.--000196), human adenovirus 12 (Genbank Accession No. AP.sub.--000141), human adenovirus 35 (Genbank Accession No. AP.sub.--000607), human adenovirus 7 (Genbank Accession No. AP.sub.--000570), human adenovirus 1 (Genbank Accession No. AP.sub.--000533), human adenovirus 11 (Genbank Accession No. AP.sub.--000474), human adenovirus 3 (Genbank Accession No. ABB 17792), and human adenovirus type 5 (Genbank accession number D12587).

In some embodiments, the polypeptides and nucleic acid molecules of the invention have the same amino acid or nucleotide sequences as those specifically recited herein or known in the art (for example in public sequence databases, such as the Genbank database). In some embodiments the polypeptides and nucleic acid molecules of the invention may have amino acid or nucleotide sequences that are variants, derivatives, mutants, or fragments of such sequences, for example variants, derivatives, mutants, or fragments having greater than 85% sequence identity to such sequences. In some embodiments, the variants, derivatives, mutants, or fragments have about an 85% identity to the known sequence, or about an 88%, 89%, 90%, 91%, 92%, 93%, 94%, 95%, 96%, 97%, 98%, or 99% sequence identity to the known sequence. In some embodiments, a variant, derivative, mutant, or fragment of a known nucleotide sequence is used that varies in length by about 50 nucleotides, or about 45 nucleotides, or about 40 nucleotides, or about 35 nucleotides, or about 30 nucleotides, or about 28 nucleotides, 26 nucleotides, 24 nucleotides, 22 nucleotides, 20 nucleotides, 18 nucleotides, 16 nucleotides, 14 nucleotides, 12 nucleotides, 10 nucleotides, 9 nucleotides, 8 nucleotides, 7 nucleotides, 6 nucleotides, 5 nucleotides, 4 nucleotides, 3 nucleotides, 2 nucleotides, or 1 nucleotide relative to the known nucleotide sequence. In some embodiments, a variant, derivative, mutant, or fragment of a known amino sequence is used that varies in length about 50 amino acids, or about 45 amino acids, or about 40 amino acids, or about 35 amino acids, or about 30 amino acids, or about 28 amino acids, 26 amino acids, 24 amino acids, 22 amino acids, 20 amino acids, 18 amino acids, 16 amino acids, 14 amino acids, 12 amino acids, 10 amino acids, 9 amino acids, 8 amino acids, 7 amino acids, 6 amino acids, 5 amino acids, 4 amino acids, 3 amino acids, 2 amino acids, or 1 amino acid relative to the known amino acid sequence.

In those embodiments where an E4ORF1 nucleic acid or amino acid sequence is used, in some embodiments such sequences are used without other sequences from the adenovirus E4 region—for example not in the context of the nucleotide sequence of the entire E4 region or not together with other polypeptides encoded by the E4 region. However, in some other embodiments such sequences may be used in conjunction with one or more other nucleic acid or amino acid sequences from the E4 region, such as E4ORF2, E4ORF3, E4ORF4, or E4ORF5 sequences, or variants, mutants or fragments thereof. For example, although E4ORF1 sequences can be used in constructs (such as a viral vectors) that contain other sequences, genes, or coding regions (such as promoters, marker genes, antibiotic resistance genes, and the like), in certain embodiments, the E4ORF1 sequences are used in constructs that do not contain the entire E4 region, or that do not contain other ORFs from the entire E4 region, such as E4ORF2, E4ORF3, E4ORF4, and/or E4ORF5.

The nucleic acid molecules of the invention can be used in constructs that contain various other nucleic acid sequences, genes, or coding regions, depending on the desired use, for example, antibiotic resistance genes, reporter genes or expression tags (such as, for example nucleotides sequences encoding GFP), or any other nucleotide sequences or genes that might be desirable. The polypeptides of the invention can be expressed alone or as part of fusion proteins.

In some embodiments nucleic acid molecules of the invention can be under the control of one or more promoters to allow for expression. Any promoter able to drive expression of the nucleic acid sequences in the desired cell type can be used. Examples of suitable promoters include, but are not limited to, the CMV, SV40, RSV, HIV-Ltr, and MML promoters. The promoter can also be a promoter from the adenovirus genome, or a variant thereof. For example, where E4ORF1 is used, the promoter can be the promoter used to drive expression of corresponding genes in an adenovirus.

In some embodiments, nucleic acid molecules of the invention can be placed under the control of an inducible promoter, so that expression of the nucleic acid sequences can be turned on or off as desired. Any suitable inducible expression system can be used, such as, for example, a tetracycline inducible expression system, or a hormone inducible expression system. For example, the nucleic acid molecules of the invention can be expressed while they are needed and then switched off when the desired outcome has been achieved, for example when there has been sufficient growth or proliferation of the endothelial cells. The ability to turn on or turn off expression could be particularly useful for in vivo applications.

The nucleic acid molecules of the invention may comprise naturally occurring nucleotides, synthetic nucleotides, or a combination thereof. For example, in some embodiments the nucleic acid molecules of the invention can comprise RNA, such as synthetic modified RNA that is stable within cells and can be used to direct protein expression/production directly within cells. In other embodiments the nucleic acid molecules of the invention can comprise DNA. In embodiments where DNA is used, the DNA sequences may be operably linked to one or more suitable promoters and/or regulatory elements to allow (and/or facilitate, enhance, or regulate) expression within cells, and may be present in one or more suitable vectors or constructs. The nucleic acid molecules of the invention can be introduced into endothelial cells in the same nucleic acid construct or they can be introduced in separate nucleic acid constructs.

The nucleic acid molecules of the invention can be introduced into endothelial cells using any suitable system known in the art, including, but not limited to, transfection techniques and viral-mediated transduction techniques. Transfection methods that can be used in accordance with the present invention include, but are not limited to, liposome-mediated transfection, polybrene-mediated transfection, DEAE dextran-mediated transfection, electroporation, calcium phosphate precipitation, microinjection, and microparticle bombardment. Viral-mediated transduction methods that can be used include, but are not limited to, lentivirus-mediated transduction, adenovirus-mediated transduction, retrovirus-mediated transduction, adeno-associated virus-mediated transduction and herpesvirus-mediated transduction.

The present invention also provides vectors, including expression vectors that contain nucleic acid molecules of the invention. For example, in one embodiment, the present invention provides an expression vector comprising a nucleotide sequence encoding an ETS transcription factor polypeptide and a nucleotide sequence encoding an E4ORF1 polypeptide. In some such embodiments the ETS transcription factor is ETV2. In some such embodiments the expression vector is a lentivirus vector. In some embodiments the nucleotide sequence encoding the ETS transcription factor polypeptide and the nucleotide sequence encoding the E4ORF1 polypeptide are under the control of separate promoters. In some embodiments the nucleotide sequence encoding the ETS transcription factor polypeptide and the nucleotide sequence encoding the E4ORF1 polypeptide are under the control of the same promoter, for example with an internal ribosome entry site sequence (IRES) between the ETS and E4ORF1 sequences.

In some embodiments a peptidomimetic may be used. A peptidomimetic is a small protein-like chain designed to mimic a polypeptide. Such a molecule could be designed to mimic any of the polypeptides of the invention (e.g. an ETV2 or E4ORF1 polypeptide). Various different ways of modifying a peptide to create a peptidomimetic or otherwise designing a peptidomimetic are known in the art and can be used to create a peptidomimetic of one of the polypeptides of the invention.

The handling, manipulation, and expression of the polypeptides and nucleic acid molecules of the invention may be performed using conventional techniques of molecular biology and cell biology. Such techniques are well known in the art. For example, one may refer to the teachings of Sambrook, Fritsch and Maniatis eds., "Molecular Cloning A Laboratory Manual, 2nd Ed., Cold Springs Harbor Laboratory Press, 1989); the series Methods of Enzymology (Academic Press, Inc.), or any other standard texts for guidance on suitable techniques to use in handling, manipulating, and expressing nucleotide and/or amino acid sequences. Additional aspects relevant to the handling or expression of E4ORF1 sequences are described in U.S. Pat. No. 8,465,732, the contents of which are hereby incorporated by reference.

Endothelial Cells

In some embodiments the present invention provides "engineered endothelial cells," such as E4ORF1+ ETV2+ engineered endothelial cells. The engineered endothelial cells can be derived from any suitable source of endothelial cells known in the art. For example, in some embodiments the endothelial cells are vascular endothelial cells. In some embodiments the endothelial cells are primary endothelial cells. In some embodiments the engineered endothelial cells are mammalian cells, such as human or non-human primate cells, or rabbit, rat, mouse, goat, pig, or other mammalian cells. In some embodiments the endothelial cells are primary human endothelial cells. In some embodiments the endothelial cells are umbilical vein endothelial cells (UVECs), such as human umbilical vein endothelial cells (HUVECs). Other suitable endothelial cells that can be used include those described previously as being suitable for E4ORF1-expression in U.S. Pat. No. 8,465,732, the contents of which are hereby incorporated by reference.

In some embodiments the engineered endothelial cells are gene-modified such that they comprise one or more genetic modifications in addition to and apart from the expression of the specific recited molecules (e.g. E4ORF1 and ETV2). For example, such cells may comprise a corrected version of a gene known to be involved in, or suspected of being involved in, a disease or disorder that affects endothelial cells, or any other gene, such as a therapeutically useful gene, that it may be desired to provide in endothelial cells or administer or deliver using engineered endothelial cells.

The engineered endothelial cells of the invention may exist in, or be provided in, various forms. For example, in some embodiments the engineered endothelial cells may comprise a population of cells, such as an isolated population of cells. In some embodiments the engineered endothelial cells may comprise a population of cells in vitro. In some embodiments the engineered endothelial cells may comprise a substantially pure population of cells. For example, in some embodiments at least about 50%, preferably at least about 75-80%, more preferably at least about 85-90%, and most preferably at least about 95% of the cells making up a total cell population will be engineered endothelial cells of the invention. In some embodiments the engineered endothelial cells may be provided in the form of a composition containing the engineered cells and one or more additional components. For example, in some embodiments the present invention may provide a composition comprising a population of engineered endothelial cells as described herein together with a carrier solution, such as a physiological saline solution, cell suspension medium, cell culture medium, or the like. In some embodiments such compositions may be therapeutic compositions—comprising a population of engineered endothelial cells and a carrier solution that is suitable for administration to a subject, such as a human subject. Other therapeutically acceptable agents can be included if desired. One of ordinary skill in the art can readily select suitable agents to be included in the therapeutic compositions depending on the intended use.

In some embodiments the engineered endothelial cells of the invention may be provided in the form of a composition (e.g. a therapeutic composition) that contains the engineered endothelial cells of the invention and one or more additional cell types. Such additional cell types may be, for example, cell types that can be maintained, cultured, or expanded in the presence of the engineered endothelial cells (e.g. using the engineered endothelial cells of the invention as "feeder" cells), or any other cell type for which it may be desired to use together with the engineered endothelial cells of the invention—for example for use in an in vitro model system or for use in co-administration to a subject. Examples of such additional cell types include, but are not limited to, stem or progenitor cells, such as hematopoetic stem or progenitor cells (HSPCs), which may be expanded using the engineered endothelial cells as "feeder" cells. Other examples of cells that can be provided or used together with the engineered endothelial cells of the invention are provided in U.S. Pat. No. 8,465,732, the contents of which are hereby incorporated by reference.

Methods and Applications

The engineered endothelial cells of the invention can be used in a variety of different applications. Similarly, the methods provided herein for making such engineered endothelial cells can be used in a variety of different settings. In general, the engineered endothelial cells provided herein can be used for any application in which non-engineered endothelial cells are currently used or could be used, or in which E4ORF1-expressing endothelial cells are currently used or could be used, such as those applications provided in U.S. Pat. No. 8,465,732, the contents of which are hereby incorporated by reference. For example, the engineered endothelial cells may be used for research purposes and/or for therapeutic purposes, for example for treatment or prevention of a disease, disorder, or condition for which administration of endothelial cells may be desired, for example an ischemic condition, such as myocardial ischemia, or some other condition that would benefit from, or be alleviated by, increased angiogenesis, for example wound healing. In the case of treatment of myocardial ischemia, the cells may be administered directly to, or in the vicinity of, the heart. In the case of treatment of wounds, the cells may be administered directly into, or in the vicinity of, the site of the wound, for example the skin in the case of a skin wound. The cells may be administered in a single dose or in multiple doses. The skilled artisan will be able to select a suitable method of administration according to the desired use.

In some embodiments, the present invention provides various therapeutic methods, such as methods for treating subjects in need thereof by administering to such subjects an effective amount of the engineered endothelial cells of the invention (or of a composition comprising such engineered endothelial cells). In such treatment methods, the cells can be administered to subjects using any suitable means known in the art. For example, the cells can be administered by injection or infusion into the blood stream or tissue at a desired location. For example, in the case of treatment of diseases, disorders, or conditions of the vascular system, engineered cells according to the present invention may be administered directly into, or in the vicinity of, the affected areas of the vascular system. In some embodiments the engineered endothelial cells may be administered together with one or more additional cell types. Such additional cell types may be, for example stem or progenitor cells, such as HSPCs and cell types that may have been genetically modified, such as genetically modified HSPCs. The engineered endothelial cells can be administered in a single dose or in multiple doses. The skilled artisan will be able to select a suitable method of administration according and a suitable dosing regimen depending on the desired use.

In some embodiments engineered endothelial cells of the present invention can be created in vivo, for example for research purposes or for therapeutic applications. For example, in some aspects, the present invention provides various therapeutic methods, such as methods for treating subjects in need thereof, which comprise administering to such subjects an effective amount of both a nucleic acid molecule that encodes an ETS transcription factor polypeptide (such as ETV2) and a nucleic acid molecule that encodes an E4ORF1 polypeptide (for example in a suitable vector, and/or under the control of a suitable promoter) such that endothelial cells in the subject are transfected or transduced with such nucleic acid molecules and become engineered endothelial cells in vivo. In such methods, the nucleotide molecules can be administered to subjects using any suitable means known in the art. For example, the nucleotide molecules (for example in a suitable vector) can be administered by injection or infusion into the blood stream or tissue at a desired location. The nucleic acid molecules can be administered in a single dose or in multiple doses. The skilled artisan will be able to select a suitable method of administration according and a suitable dosing regimen depending on the desired use.

In some embodiments the engineered endothelial cells of the invention are mitotically inactivated prior to use (e.g. therapeutic use) such that they cannot replicate. This can be achieved, for example, by using a chemical agent such as mitomycon C or by irradiating the engineered endothelial cells.

Cell Culture Methods

Methods of culturing cells are well known in the art and any suitable cell culture methods can be used. For example, the engineered endothelial cells of the invention can be cultured using methods known to be useful for culturing other endothelial cells, or, methods known to be useful for culturing E4ORF1-expressing endothelial cells, for example as described in U.S. Pat. No. 8,465,732, the contents of which are hereby incorporated by reference. In some embodiments the engineered endothelial cells of the invention can be cultured in the absence of serum, or in the absence of exogenous growth factors, or in the absence of both serum and exogenous growth factors. The engineered endothelial cells of the invention can also be cryopreserved. Various methods for cell culture and cell cryopreservation are known to those skilled in the art, such as the methods described in Culture of Animal Cells: A Manual of Basic Technique, 4th Edition (2000) by R. Ian Freshney ("Freshney"), the contents of which are hereby incorporated by reference.

In some embodiments, the present invention provides feeder cells, conditioned medium, and cell products that comprise, or are derived from, the engineered endothelial cells of the invention and that can be useful to support the survival or growth of other cells types, for example in a co-culture method. For example, in one embodiment a population of engineered endothelial cells can be used as feeder cells to support the growth of stem or progenitor cells, such as HSPCs and HSPCs that have been genetically modified. Similarly, in other embodiments the present invention may provide conditioned cell culture medium obtained from a culture of engineered endothelial cells of the invention, or cell products (such as total cell lysates, cell fractions, or specific cell products) obtained from a culture of engineered endothelial cells of the invention.

In some embodiments the present invention provides co-culture methods for culturing a population of cells of interest. Such "cells of interest" include, but are not limited to, cancer cells (such as primary cancer cells, cancer stem cells and cancer cell lines), hybridoma cells, stem or progenitor cells (such as embryonic stem cells, induced pluripotent stem cells (IPSCs), and stem cells derived from any fetal or adult tissues such as hematopoietic stem cells, neural stem cells, skin stem cells, spermatogonial stem cells, gut stem cells, and cancer stem cells, and the like), and other cell types that are typically cultured using feeder cells, or for which it is desired to use a feeder-cell culture system. Such co-culture methods may comprise culturing a population of cells of interest and a population of the engineered endothelial cells of the invention together in the same culture vessel. In some such embodiments the engineered endothelial cells may form a feeder cell layer on a surface of the culture vessel, and the cells of interest may be placed on the feeder cell layer. In another embodiment the present invention provides a method of culturing cells of interest comprising: contacting a population of cells of interest with conditioned medium obtained from a culture of the engineered endothelial cells of the invention. In some embodiments the present invention also provides conditioned cell culture medium obtained from a culture of engineered endothelial cells of the invention.

Kits

The present invention also provides kits for carrying out the various methods described herein or for producing the engineered endothelial cells provided herein. Such kits may contain any of the components described herein, including, but not limited to, nucleotide sequences (for example in a vector), endothelial cells, populations of engineered endothelial cells, control non-engineered endothelial cells, sample/standard engineered endothelial cells, means or compositions for detection of engineered endothelial cells or the proteins or nucleic acid molecules expressed therein, (e.g. nucleic acid probes, antibodies, etc.), media or compositions useful for maintaining or expanding engineered endothelial cells, media conditioned by engineered endothelial cells, means or compositions for administering engineered endothelial cells to a subject, or any combination thereof. All such kits may optionally comprise instructions for use, containers, culture vessels and the like. A label may accompany the kit and may include any writing or recorded material, which may be electronic or computer readable form (e.g., disk, optical disc, memory chip, or tape) providing instructions or other information for use of the kit contents.

Certain aspects of the present invention may be further described in the following non-limiting Example.

EXAMPLE

Generation and Use of E4ORF1+ETV2+ Endothelial Cell

Figure 1:
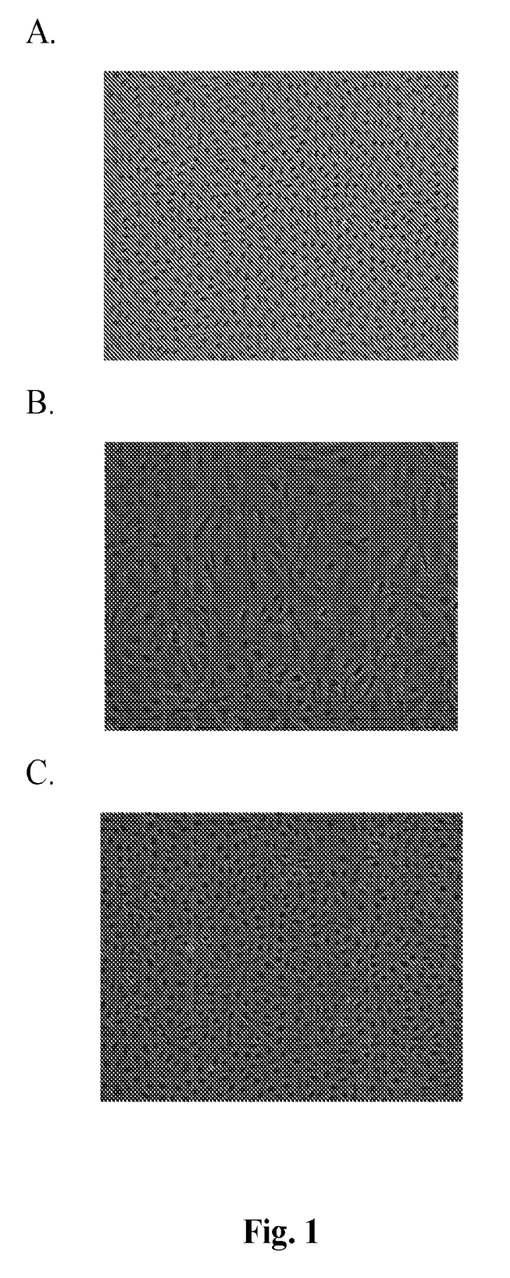
FIGS. 1A-1C show phase microscopy images of E4ORF1+ETV2− (FIG. 1A), E4ORF1−ETV2+ (FIG. 1B), and E4ORF1+ETV2+ (FIG. 1C) engineered endothelial cells at passage 8 (7 passages after transduction).

Human umbilical vein endothelial cells (HUVECs) were engineered to express either (a) E4ORF1 alone (E4ORF1+ ETV2−), (b) ETV2 alone (E4ORF1−ETV2+), or (c) both E4ORF1 and ETV2 (E4ORF1+ETV2+). Nucleic acid molecules encoding adenovirus E4ORF1 were introduced into the HUVECs in a lentiviral vector, as described previously in Seandel et al., PNAS, 2008; 105(49): pp. 19288-93, the contents of which are hereby incorporated by reference. Nucleic acid molecules encoding human ETV2 (Genbank accession no. NM 01429) were introduced using the same lentiviral system (two separate lentiviral constructs were used—one for E4ORF1 and one for ETV2). Lentivirus was delivered at a multiplicity of infection (MOI) of 1-5. ETV2 expression was confirmed by PCR. E4ORF1 expression was confirmed phenotypically (as has been reported previously, E4ORF1+ endothelial cells can survive in serum free media, while E4ORF1− endothelial cells die in serum free conditions. The engineered endothelial cells were cultured in serum-containing M199 media (10% FBS) with antibiotics, HEPES, FGF2 cytokine, heparin, and Glutamax and maintained for 2-15 passages. If cells were in a single flask for at least 48-72 hours without splitting, the culture medium was exchanged. It was found that the E4ORF1−ETV2+ endothelial cells (i.e. those expressing ETV2 but not E4ORF1) behaved similarly to non-transduced (E4ORF1−ETV2−) endothelial cells, in that they could not be maintained in culture for multiple passages, but rather began to senesce in culture and lose their endothelial cell phenotype. However, the E4ORF1+ETV2+ endothelial cells could be cultured for many more passages without senescence and continued to actively proliferate without loss of their endothelial cell phenotype, even in serum-free conditions. FIG. 1 shows micrographs of E4ORF1+ETV2− (FIG. 1A), E4ORF1− ETV2+ (FIG. 1B), and E4ORF1+ETV2+ (FIG. 1C) engineered endothelial cells at passage 8 (7 passages after lentiviral transduction). It can be seen that the E4ORF1− ETV2+ endothelial cells appear to be undergoing senescence, while the E4ORF1+ETV2− and E4ORF1+ETV2+ endothelial appear to be healthy and non-senescent. The E4ORF1−ETV2+ cells showed no proliferative differences compared to naïve E4ORF1−ETV2− endothelial cells. The E4ORF1−ETV2+ endothelial cells grew at approximately the same rate as the E4ORF1+ETV2− cells for the first 2-3 passages, following which the proliferation decreased until eventual senescence at around passage 8-10.

The various engineered endothelial cells were allowed to grow to confluence and then switched to hematopoietic media without cytokine supplement (Stemspan™ media from StemCell Technologies) overnight—before commencing co-culture with human hematopoietic stem and progenitor cells (HSPCs). HSPCs were obtained from the buffy coat of umbilical cord blood. CD34+ HSPCs were purified from the buffy coat sample using magnetic columns from Miltenyi Biotech. The CD34+ HSPCs cells were then added to the endothelial cell cultures with a 50 ng/ml bolus of cytokines (tpo/flt3l/scf). A "cyto alone" control group of HSPCs were treated in the same way (with the same cytokine treatment) but were not co-cultured with endothelial cells.

Figure 2:
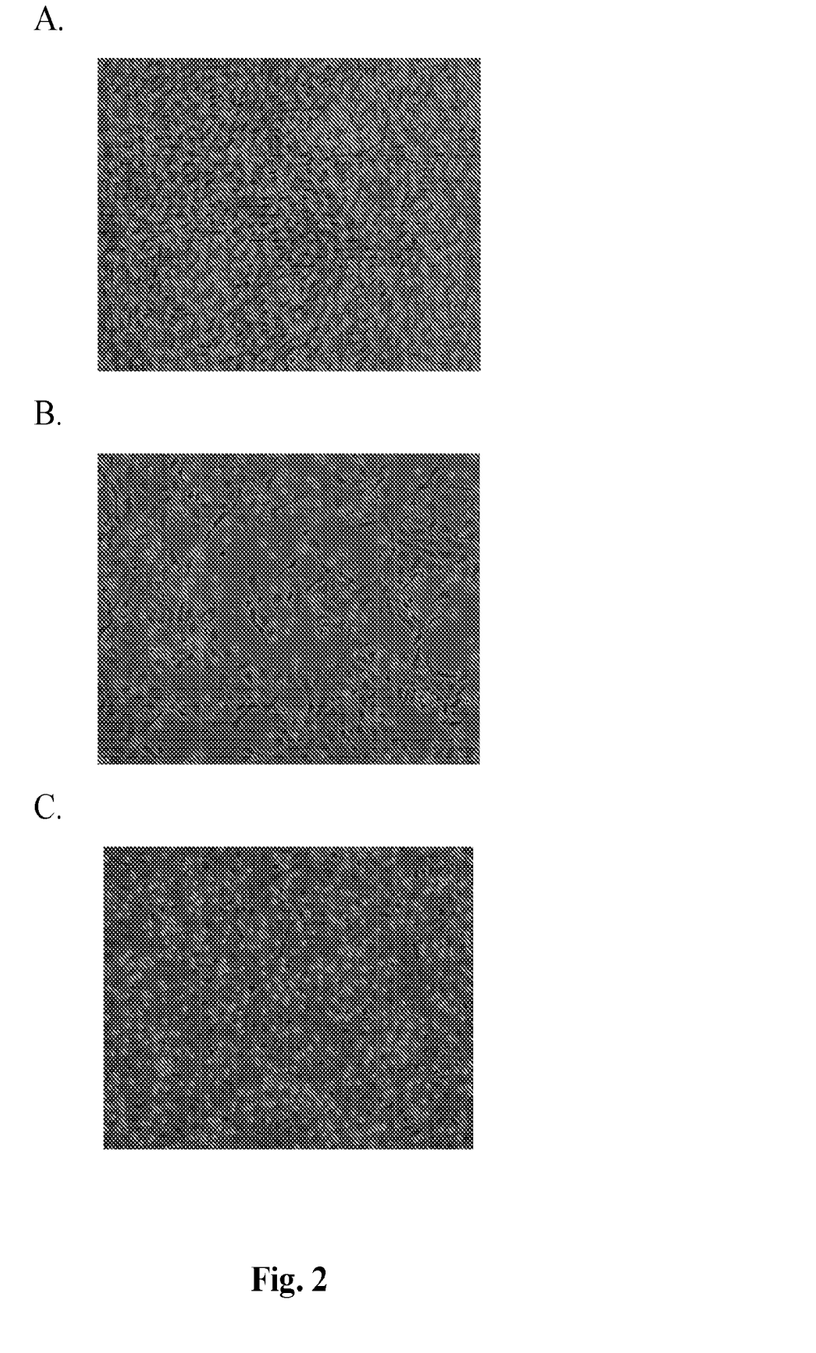
FIGS. 2A-2C show phase microscopy images of E4ORF1+ETV2− (FIG. 2A), E4ORF1−ETV2+ (FIG. 2B), and E4ORF1+ETV2+ (FIG. 2C) endothelial cells, after 10 days in co-culture with HSPCs.

FIG. 2 shows micrographs of E4ORF1+ETV2− (FIG. 2A), E4ORF1−ETV2+(FIG. 2B), and E4ORF1+ETV2+ (FIG. 2C) endothelial cells after 10 days in co-culture with the HSPCs. Endothelial cells expressing ETV2 alone (E4ORF1−ETV2+) underwent significant cell death during the HSPC co-culture and expansion process, while the endothelial cells expressing E4ORF1 alone (E4ORF1+ ETV2−), or both ETV2 and E4ORF1 (E4ORF1+ETV2+), remained alive and mostly confluent for the majority of the co-culture and expansion process, even in the presence of the serum free media. After 10 days of co-culture measurements of total cell counts were made and flow cytometry was performed using CD34, CD45RA, CD38, and CD49F markers. This allowed calculation of the number of CD34+ cells as a percentage out of the total numbers of cells or as a percentage of the total number of CD45+ cells.

Figure 3:
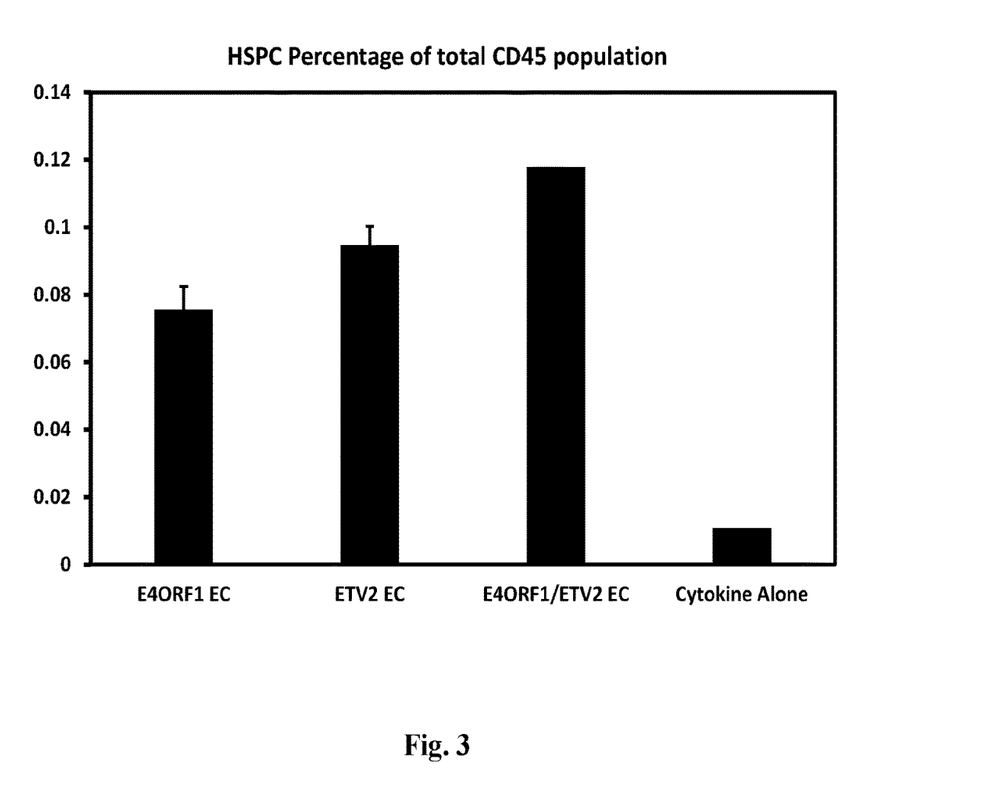
FIG. 3 shows the effects of endothelial cells engineered to express either E4ORF1 alone (E4ORF1+ETV2−), ETV2 alone (E4ORF1−ETV2+), or both E4ORF1 and ETV2 (E4ORF1+ETV2+) (as indicated by the bar labels on the x axis) on co-cultured HSPCs. Cells were co-cultured for 10 days. The y axis represents numbers of CD34+ HSPCs presented as a percentage of number of CD45+ cells.

The data from this experiment is provided in FIG. 3. It was found that, while the endothelial cells-expressing E4ORF1 alone promoted expansion of CD34+ HSCs (as has been demonstrated previously), endothelial cells expressing both E4ORF1 and ETV2 were even more effective—leading to even greater expansion of CD34+ HSCs than was achieved using E4ORF1 alone. This difference in HSPC expansion between the E4ORF1+ETV2− and E4ORF1+ETV2+co-culture groups was statistically significant. Furthermore, it was found that the combination of E4ORF1 and ETV2 together led to a greater expansion of "more primitive" HSPCs than was observed when either E4ORF1 or ETV2 were used alone—where the "more primitive" HSPCs were CD34+high, CD45RA− (and also CD38−, CD49F+). The less primitive HSPCs were CD45RA+ and either CD34+high (less primitive) or CD34+ (even less primitive). (The more primitive the HSPCs the higher the CD34 expression). Although it was found that endothelial cells expressing ETV2 alone (E4ORF1−ETV2+) could expand CD34+ HSPCs to some degree in the experiments described here, in view of the significant senescence and cell death observed such cells would likely be problematic for larger scale applications, such as clinical applications. On the other hand, endothelial cells expressing both E4ORF1 and ETV2 (E4ORF1+ETV2+), which do not suffer from these problems, could provide a unique and valuable source of endothelial cells for applications requiring large-scale endothelial cell culture or large-scale endothelial cell co-culture, including clinical applications.

The present invention is further described by the following claims.

We claim:

1. An isolated composition comprising E4ORF1+ ETV2+ engineered human umbilical vein endothelial cells (HUVECs) and hematopoietic stem or progenitor cells (HSPCs), wherein the HUVECs do not comprise an entire adenovirus E4 region.

2. The composition of claim 1, wherein the HUVECs comprise a recombinant nucleic acid molecule that encodes an ETV2 polypeptide, an adenovirus E4ORF1 polypeptide, or both an ETV2 polypeptide and an adenovirus E4ORF1 polypeptide.

3. The composition of claim 2, wherein the nucleic acid molecule is in the form of a plasmid vector.

4. The composition of claim 2, wherein the nucleic acid molecule is not integrated into the genomic DNA of the engineered HUVECs.

5. The composition of claim 2, wherein the nucleic acid molecule is integrated into the genomic DNA of the engineered HUVECs.

6. A composition according to claim 1 further comprising a carrier solution suitable for administration to a subject.

7. A composition according to claim 6 for use in a cell transplantation procedure.

8. A composition according to claim 6 for use in an HSPC transplantation procedure.

9. The composition of claim 1, wherein the HUVECs do not comprise adenovirus E4ORF2, E4ORF3, E4ORF4, and/or E4ORF5.

10. A method of maintaining or expanding a population of hematopoietic stem or progenitor cells (HSPCs) in culture, the method comprising: culturing a population of E4ORF1+ ETV2+ engineered human umbilical vein endothelial cells (HUVECs) in the same culture vessel as a population of HSPCs.

11. The method of claim 10, wherein the engineered HUVECs form a feeder cell layer on the surface of the culture vessel.

12. The method of claim 10 wherein the culturing is performed in the absence of serum.

* * * * *